US007188625B2

United States Patent
Durette

(10) Patent No.: US 7,188,625 B2
(45) Date of Patent: Mar. 13, 2007

(54) OCULAR SURGICAL PROTECTIVE SHIELD

(76) Inventor: Jean-Francois Durette, 1170 East Henri-Bourassa Blvd., Montreal, Quebec (CA) H2C 1G4

( * ) Notice: Subject to any disclaimer, the term of this patent is extended or adjusted under 35 U.S.C. 154(b) by 335 days.

(21) Appl. No.: 10/605,992

(22) Filed: Nov. 12, 2003

(65) Prior Publication Data

US 2006/0243286 A1    Nov. 2, 2006

(51) Int. Cl.
*A61F 9/00* (2006.01)
(52) U.S. Cl. .............. 128/858; 250/515.1; 250/516.1; 351/44; 2/431; 2/432
(58) Field of Classification Search ............. 128/857, 128/858; 2/431, 432, 12, 15; 250/515.1, 250/516.1; 351/41, 44
See application file for complete search history.

(56) References Cited

U.S. PATENT DOCUMENTS

| 2,283,752 | A |   | 5/1942 | Gonsett |
| 4,024,405 | A | * | 5/1977 | Szot ..................... 250/516.1 |
| 5,390,373 | A | * | 2/1995 | Flory ............................ 2/430 |
| 5,918,600 | A |   | 7/1999 | Durette |
| 6,081,934 | A | * | 7/2000 | Stefanovsky et al. .......... 2/431 |
| 6,123,081 | A |   | 9/2000 | Durette |

* cited by examiner

Primary Examiner—Henry Bennett
Assistant Examiner—Camtu Nguyen
(74) Attorney, Agent, or Firm—Ryan N. Carter

(57) ABSTRACT

External ocular shields for protecting a patient's eyes from medical treatment radiation energy such as a laser during a medical procedure. Each shield has an external surface that absorbs energy that hits the shield. The shields are connected to each other by a nose piece, and the nose piece is connected to each shield by a mounting means. The mounting means are positioned perpendicular to the shields and parallel to each other so that the nose piece can pivot upward towards the user's forehead and downward towards the user's chin without altering the fit of the shields over the user's eyes.

33 Claims, 10 Drawing Sheets

FIG. 13
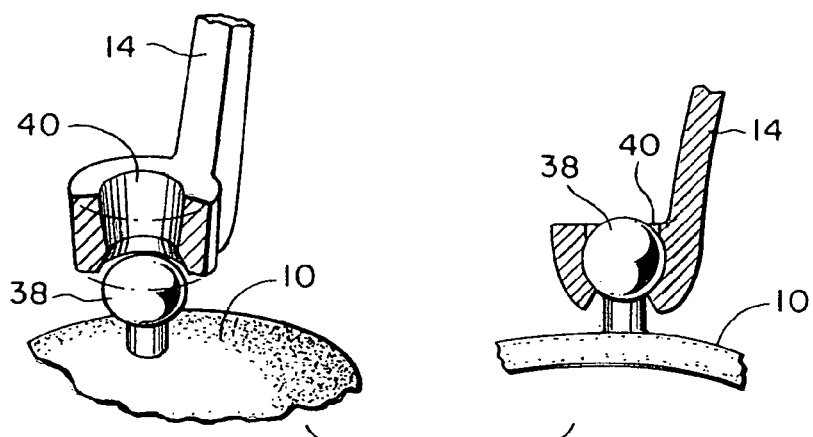
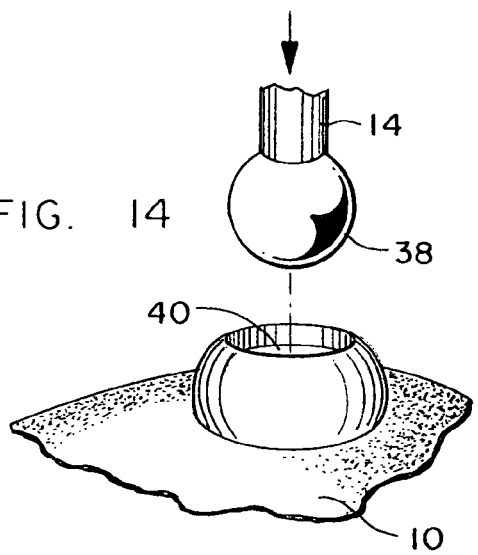
FIG. 14
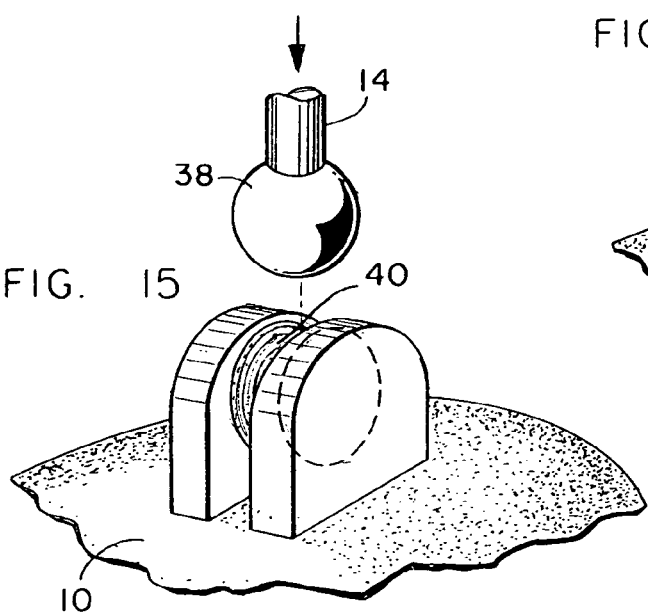
FIG. 15
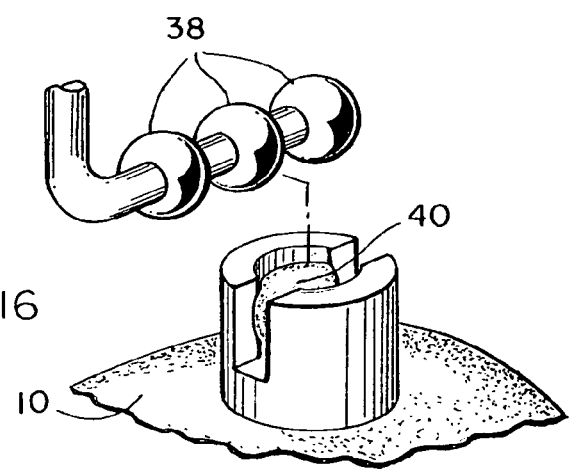
FIG. 16

OCULAR SURGICAL PROTECTIVE SHIELD

BACKGROUND OF INVENTION

Lasers and other various energy types are being used with increasing frequency in a variety of medical procedures. Although lasers make many procedures easier, less painful, and more precise, there are also certain risks associated with using lasers on patients. A primary risk associated with using lasers is the danger of getting laser light in a person's eyes. Even a brief shot of laser light into a person's eyes can cause serious damage and even blindness. Another risk associated with high powered energy devices is that the radiant energy may hit the eye shield and transform into heat energy, thus burning the patient where the eye shield contacts the patient's skin. In medical procedures a specialist must be careful that an inadvertent beam of radiation does not enter a patient's eyes or hit the shield repeatedly to cause the shield to heat up, especially if the specialist is working on a patient's head or face.

In order to minimize this risk, ocular shields have been used to protect the patient's eyes so as to diffuse laser energy that might be inadvertently aimed at the patient's eyes. There are several ocular shields known at the present time. One shield is inserted behind the lids over the patient's eyes. These shields must be the proper size so as to cover the entire globe. Although smaller shields are easier to insert and remove, it is important that the entire globe be covered especially during periorbital surgery. Because of the possibility of discomfort and necessity of inserting shields of this type to protect the eyes, surgeons sometimes use either plastic suntan goggles or simply wet gauze placed over the eyes when not working near the ocular globe. However, when the procedure is closer to the eye, the ocular shields must be inserted beneath the lids in order to provide adequate protection.

Another type of shield is an external ocular protective device shown in U.S. Pat. No. 5,918,600. This shield is a protective device that fits over both eyes with a wire piece connecting both protective shields. In this device, the wire connecting the shields may get in the way when the specialist works on certain areas of the face, especially near the bridge of the nose. U.S. Pat. No. 2,283,752 discloses ocular shields connected by a movable wire. However, the problem with this shield is that when the wire is moved upward or downward so it does not interfere with the specialists procedure, the angle and fit of the shields changes on the patient's face, potentially allowing radiation to reach the patient's eyes. This problem is shown in FIG. 19 of the drawings of this application.

Therefore, there is a need for improved external ocular shields that allow the nose piece to be moved without changing the angle or fit of the shields. Any such ocular shields should be autoclavable and totally non-reflective to the medical treatment radiation energy so as to prevent the energy from passing through and reflecting back onto the surgeon or other personnel in the operating room.

SUMMARY OF INVENTION

The present invention is a device that shields a person's eyes from different forms of radiation. The invention is illustrated primarily as used for eye protection from laser energy, however, it is to be understood that the present invention can be used to protect a person's eyes from all forms of radiation energy including the sun, as well as all forms of medical treatment radiation energy including but not limited to lasers, radio frequencies, medical dermabrasion granules, micro waves, and intense pulse light. The eye shields have an external surface that absorbs any laser energy that hits the shield. The shields are connected to each other by a nose piece and the nose piece is connected to each shield by a mounting means. The mounting means is combined with the nose piece securely enough that involuntary movement of the nose piece relative to the shields is retarded, while voluntary movement of the nose piece is allowed. The shields and nose piece can be made of metal or plastic, depending on what procedure is being performed and what type of energy is being used. The nose piece can pivot through a range of positions using the mounting means as its pivot point. This displacement of the nose piece is desirable so that the nose piece does not block a specialist's access to any particular area of the patient's face. However, as the specialist displaces the nose piece, the shields do not change their position on the patient's face which could allow radiant energy to inadvertently pass under the shields and into the patient's eyes. In order to keep the shields stationary as the nose piece is moved, each mounting is positioned substantially perpendicular to its shield and the mounting on the first shield is positioned parallel to the mounting on the second shield so that the mounting on the first shield is a mirror image of the mounting on the second shield. This alignment allows the nose piece to be displaced upward toward the patient's forehead and downward toward the patient's chin without affecting the fit or position of the shields over the patient's eyes. As will be obvious from the description below, many of the means used to connect the nose piece with the shields can also be used in the temporal area of the shields to connect the shields to the headband which holds the shields to the patient's face.

BRIEF DESCRIPTION OF DRAWINGS

FIG. 13 is a perspective view of a ball and socket mounting means with the ball on the shield and the socket on the nose piece;

FIG. 14 is a perspective view of a variation of the ball and socket mounting means with the ball on the nose piece and the socket on the shield;

FIG. 15 is a perspective view of a variation of the ball and socket mounting means with the ball on the nose piece and the socket on the shield;

FIG. 16 is a perspective view showing a variation of the ball and socket mounting means with multiple balls on the nose piece for maximum adjustability;

DETAILED DESCRIPTION

Figure 1:
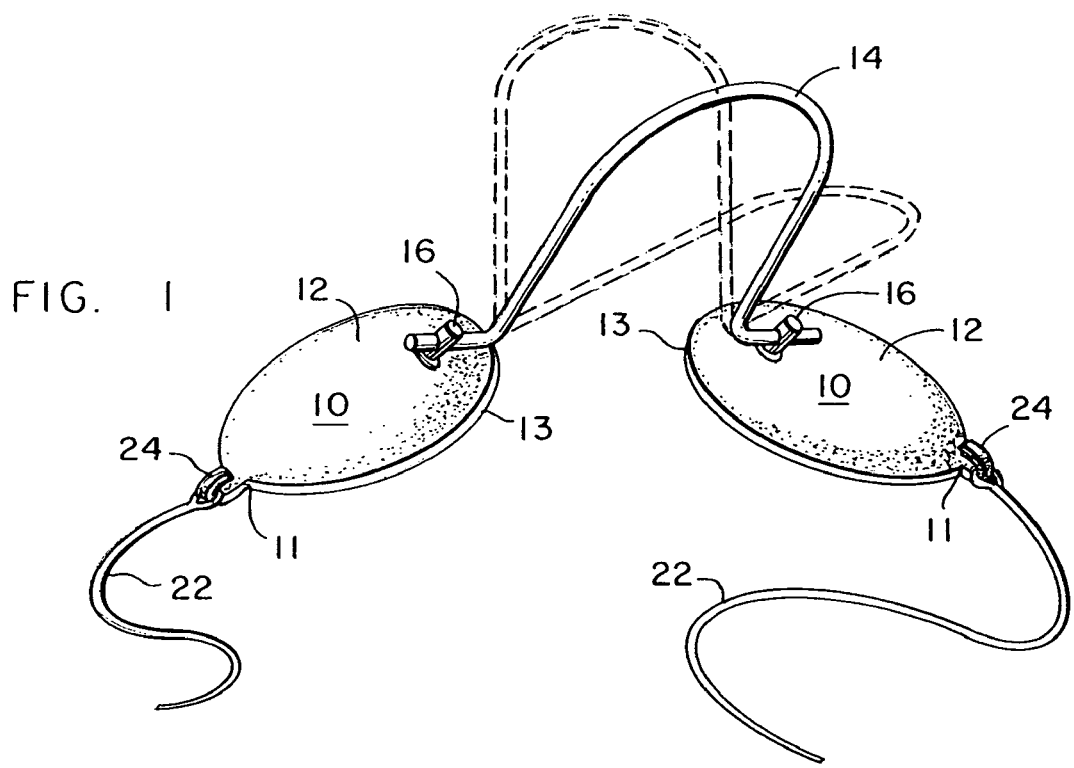
FIG. 1 is a front perspective view showing the ocular shields and the movement of the nose piece without any displacement of the shields.

FIG. 1 shows how the external ocular shield device is comprised of two shields 10 connected by a nose piece 14. The shields 10 and nose piece 14 can be made of metal, plastic, or a combination of metal and plastic, depending on which procedure is being preformed and which type of energy is being used. Each shield 10 is sized and shaped so that it will cover the entire eye. Each shield 10 comprises an outer temporal area 11 and an inner nasal area 13, and can further comprise an elastomeric lip 46 (shown in FIG. 18) that can be molded onto the shields 10 so as to provide a comfortable and precise fit around the patient's eyes. The elastomeric lip 46 further serves to keep any heat energy that may build up on the shield 10 from contacting the patient's skin. The shields 10 are approximately 1 mm 4 mm thick and are constructed of a material that does not allow medical treatment radiation energy to pass through. In one embodiment the shields are constructed of a metal such as stainless steel, or titanium. Both the shields 10 and the nose piece 14 may have an outer surface 12 that has been treated to be non-reflective so that it does not allow the laser energy to be reflected onto the surgeon or other personnel in the room. Such surface treatments to make metals non-reflective are well known in the art. Alternatively, the shields 10 may not be treated, yet be suitable to diffuse, block, or absorb the energy. For example, where the shields are plastic or rubber, a non-reflective coating may not be needed.

The present invention contains several embodiments for fastening the shields 10 onto a patient's face, all of which allow comfort and flexibility. As seen in FIG. 1, the outer temporal area 11 of each shield 10 has an attachment hook 24. In this embodiment, an elastic headband 22 is attached to each hook 24 and placed around and behind the patient's head to hold the ocular shield device over the patient's eyes.

The elastic head band 22 is easily removable from the attachment hooks 24 so that it can be separately sterilized. Also, since the elastic headband 22 can become damaged if hit by laser radiation, the elastic head band 22 can be easily removed and replaced.

Figure 20:
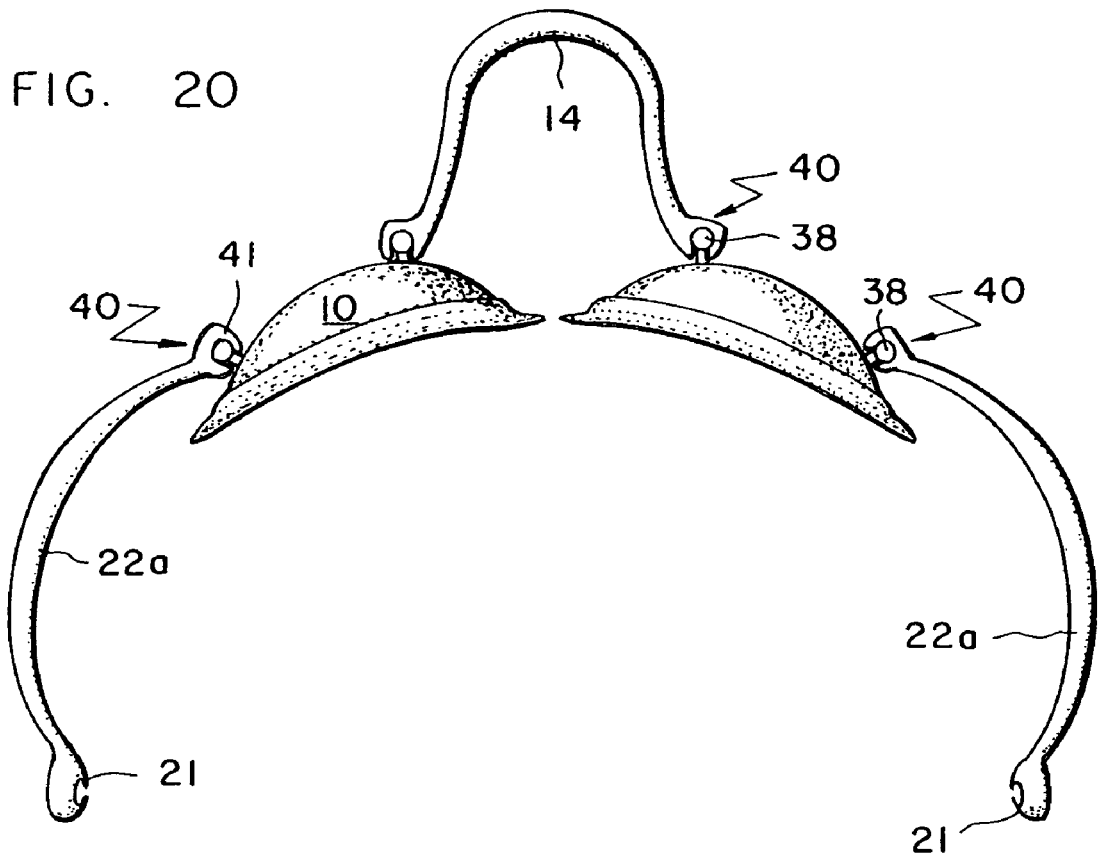
FIG. 20 is a top view of the present invention showing how the nose piece and the band adapted to be placed around and behind the patient's head can be attached to the shields using a ball and socket joint.
Figure 21:
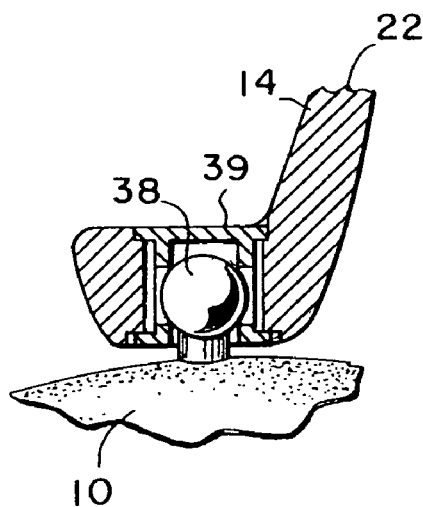
FIG. 21 is a cross-sectional view of a ball and socket joint with a plastic liner to hold the ball in place.
Figure 23:
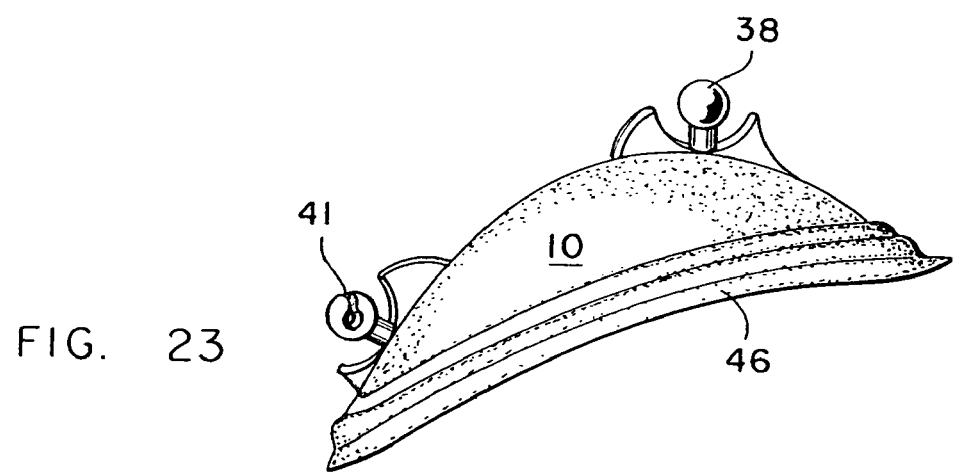
FIG. 23 is a side view of a shield with two ball bearings on it and the temporal ball bearing having a notch for insertion of an elastic head band.

In an alternative embodiment shown best in FIG. 20, the head band is comprised of two separate flexible rubber or plastic headband components 22a that attach to the shield 10 with a ball and socket joint. On each plastic headband component 22a, the end opposite the socket 40 comprises a means 21 for connecting the corresponding means 21 to the other plastic headband component 22a when placed around and behind the patient's head. The flexible material of the plastic headband component 22a allows the attachment of this embodiment to be adjustable. The socket 40 end of each flexible plastic headband component 22a attaches onto a ball 38 located on the shield 10 forming a ball and socket joint at their juncture. The ball and socket can be separated for cleaning purposes. The ball 38 on the shield 10 can be metal or plastic. If the ball 38 is metal, there is preferably a plastic liner 39 in the socket 40 to help hold the ball 38 in place as shown in FIG. 21. As shown in FIG. 23, the ball 38 on the outer temporal area 11 of the shield 10 has a notch 41 in it so that if the flexible plastic headband component 22a comprising the socket 40 is not desired, an elastic band 22 can be used as described in the previous paragraph.

Figure 22:
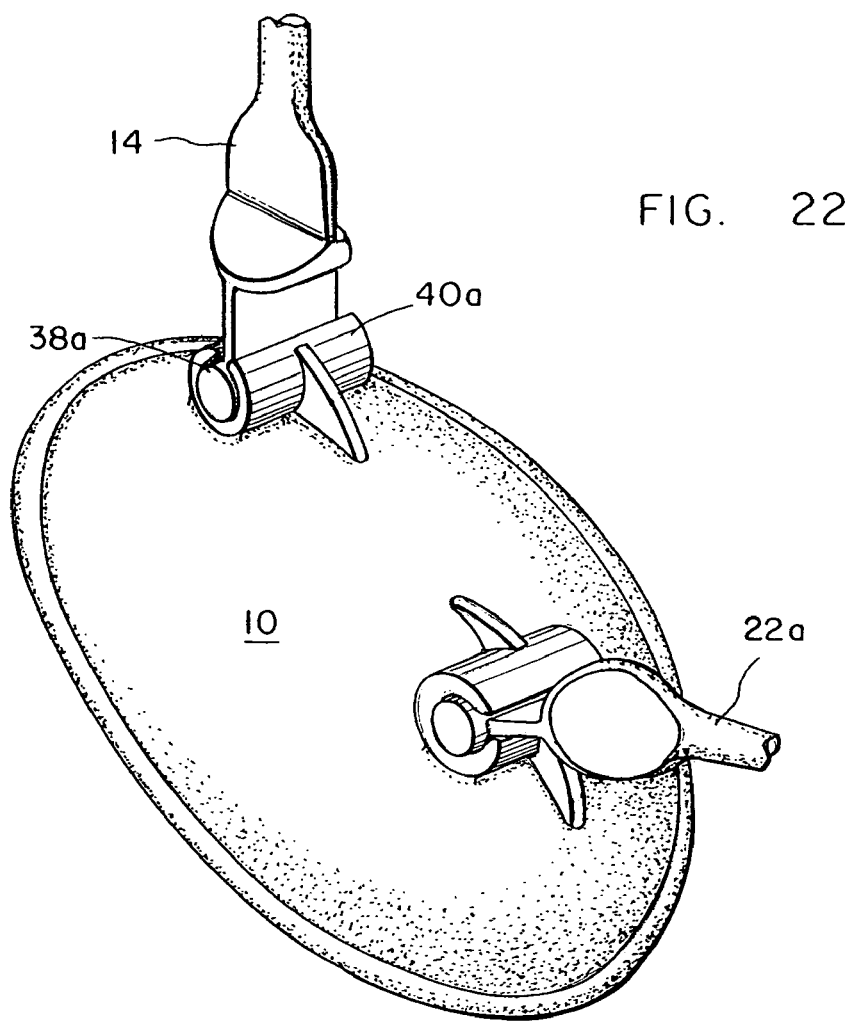
FIG. 22 is a perspective view of a hinge attachment means.

FIG. 22 shows a variation to the ball and socket embodiment where a cylindrical hinge 38a combines with a hinge-type cylindrical socket 40a to connect the nose piece 14 and/or the plastic headband component 22a to the shield 10.

In yet another alternative embodiment, an elastic band 22 is not needed to hold the shields 10 in place over the patient's eyes. In this embodiment, the weight of the ocular shield device is increased, and its weight is enough to hold the shields 10 on the patient's face. This embodiment is useful when the specialist is working on wrinkles located on either side of the patient's eyes (where the elastic band 22 is located in the previous embodiment).

In yet another alternative embodiment, the elastic head band 22 attaches to temporal wires instead of the attachment hooks 24. Such wires are described in U.S. Pat. No. 5,918,600. These temporal wires extend outwardly and away from the face to allow the specialist to work on the sides of the face without any interference from the elastic band 20. Preferably, these temporal wires attach to the shields 10 perpendicularly so that they can be moved upward and downward without upsetting the placement of the shields 10 over the eyes. This attachment of the temporal wires with the shield 10 is similar to the attachment of the nose piece 14 with the shield 10 as described below. Any other suitable means for attaching the ocular shield device onto a patient's head is meant to be included within the scope of this invention.

It is important that a specialist be able to perform surgery on any area of the face while the patient is wearing the ocular shield. In this regard, the nose piece 14 must not interfere or block the specialist's access to the patient's face. FIG. 1 shows how the nose piece 14 extends generally outwardly from the shields 10 so as to provide adequate space beneath and around the nose piece 14 for the surgeon to perform medical procedures without interference from the nose piece 14. The nose piece 14 attaches to each shield 10 by way of a mounting 16. To allow access to all areas of a patent's face, the nose piece 14 is movable using the mounting 16 as its pivot point. As illustrated in FIG. 1, the mounting 16 is such that it allows the nose piece 14 to be moved from a first position to a second position, and remain in the second position without assistance from the specialist. It is desirable for a specialist to be able to move the nose piece 14 if it gets in the way during a procedure, however, when the nose piece 14 is moved it must not change the fit of the shields 10 over the eyes. If the shields 10 shift position as the nose piece 14 is moved, laser energy may inadvertently get under the shields 10 and into the patient's eyes.

Figure 19:
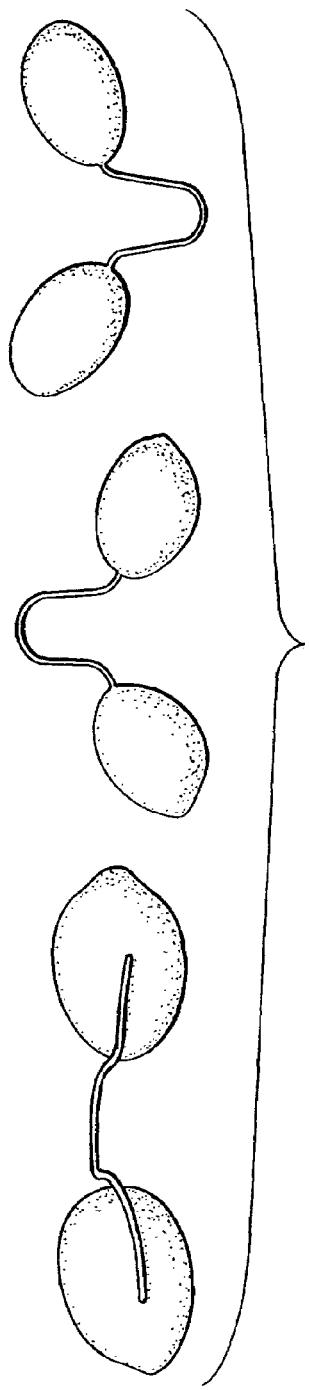
FIG. 19 is a series of three drawings showing the prior art problem in which the shields move as the nose piece changes position.

To allow the nose piece 14 to move without moving the shields 10, precise alignment of both of the mountings 16 relative to each other is required. The mounting 16 on the first shield 10 is positioned parallel to the mounting 16 on the second shield 10 so that the mountings 16 are mirror images of each other. The nose piece 14 connects with the first shield 10 at the same angle that it connects with the second shield 10. This alignment of the mountings 16 and nose piece 14 allows the nose piece 14 to pivot upward toward the patient's forehead and downward toward the patient's chin without changing the angle or fit of the shields 10 on the patient's face. This is distinguished from the prior art, as shown in FIG. 19, in which the eye shields change position as the nose piece is moved upward and downward, which could potentially allow laser radiation into a patient's eyes.

Figure 2:
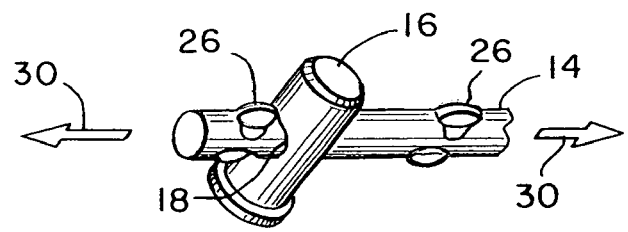
FIG. 2 is a perspective view of the nose piece passing through the hole in the post mounting means with flanges on the nose piece to prevent it from coming out of the hole.
Figure 3:
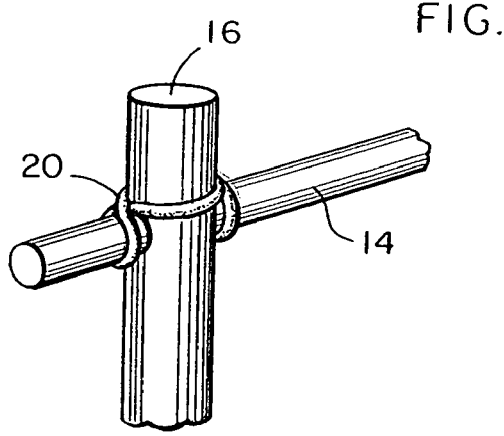
FIG. 3 is a perspective view of the nose piece connecting to the post mounting means with elastic bands.

FIGS. 2 and 3 show a mounting in which the mounting 16 is a post that is attached perpendicularly to the shield 10. The mounting post 16 can be positioned anywhere on the surface of the shield 10, as long as it is a mirror image of the mounting post 16 on the other shied 10. Each mounting post 16 has a post hole 18 through which the nose piece 14 is inserted. The outer ends of nose piece 14 have flared flanges 26 formed on them to retain the hose piece in the post holes 18. The post hole 18 in the mounting post 16 on the first shield is parallel to the post hole 18 in the mounting post 16 on the second shield 10. The nose piece 14 can be any shape and length, as long as it fits perpendicularly into each mounting post 16, and remains parallel to the hole 18 for a short distance on either side of the hole 18. The shields 10 can also adjust linearly along the nose piece 14 to adjust the size of the device.

Figure 9:
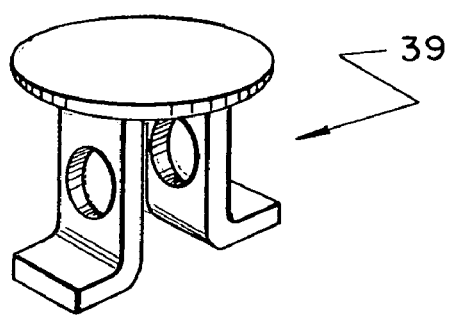
FIG. 9 is a perspective view of a plastic insert for insertion into the socket of a ball and socket joint.

Additional embodiments for attaching the nose piece 14 to the shields 10 while still allowing adjustability to the ocular shield device are shown with different variations in FIGS. 11–15, 20, and 21, and 23. These mountings employ a ball and socket joint where the nose piece 14 meets the post 16 or shield 10. A ball 38 connects into a socket 40. The socket 40 fits tightly around the ball 38 so that there remains enough friction in the joint to retard involuntary movement, but still allow voluntary movement of the nose piece 14. The ball 38 may be inserted into the socket 40 by snapping the ball 38 into a flexible socket 40, or, a plastic liner 39 may be inserted into a rigid socket 40 to hold the ball 38 tightly in place as shown in FIG. 21. Because metal is not very flexible, this plastic liner 39 is particularly important in the embodiments that employ a metal ball and a metal socket. In these metal to metal embodiments, the plastic liner 39 acts as a buffer in that it allows the metal ball 38 to snap into and move easily within the socket 40. A perspective view of the plastic liner 39 is seen in FIG. 9, while the plastic liner 39 is seen as positioned inside the ball and socket joint in FIG. 21.

Figure 24:
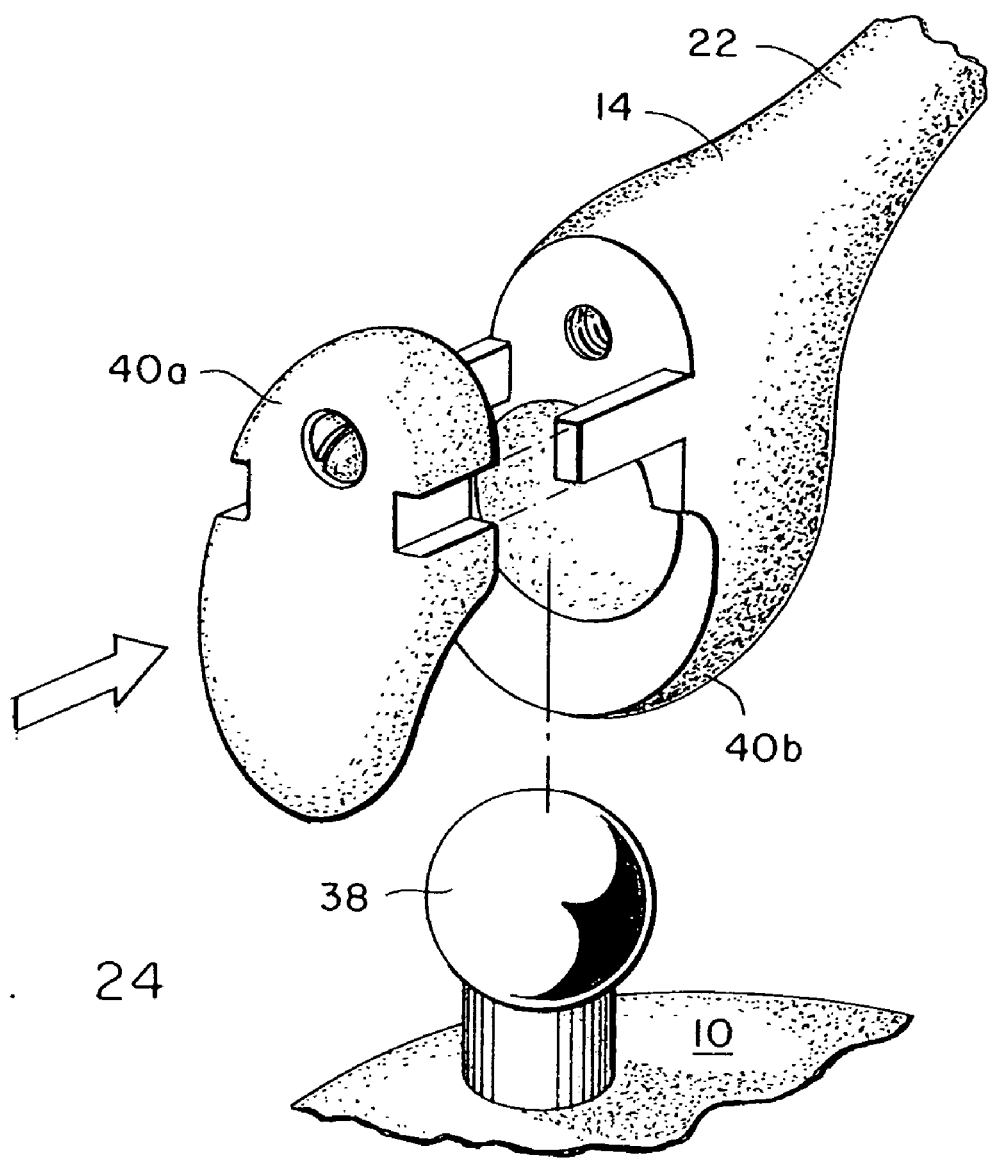
FIG. 24 is a perspective view of a ball and socket joint where the socket attaches around the ball.

Another embodiment for inserting and retaining the ball 38 in the socket 40 is shown in FIG. 24 wherein the socket 40 is comprised of two separate components that attach around the ball 38. In this embodiment, the ball 38 does not snap into the socket 40, rather the socket 40 attaches around the ball 38. The first component 40a snaps or screws together with the second component 40b.

The ball and socket embodiments allow universal adjustability of the nose piece 14 while still allowing restricted movement of the shields 10. As shown in FIGS. 14, 15, and 16 the ball 38 is on the nose piece 14 and the socket 40 located on the shield 10. FIG. 16 shows how the nose piece 14 can contain several different balls 38 spaced at different points along the nose piece 14 to allow for further adjustability. The reverse is shown in FIGS. 11, 12, 13, 20, and 21 wherein the ball 38 is on the shield 10 and the socket 40 is on the nose piece 14. FIG. 13 shows how there can be several sockets 40 for the ball 28 to fit into for maximum adjustability.

The same concepts of a ball and socket attachment means can be employed to fasten the shields 10 onto the patient's face using the headband 22 or 22a.

In yet another embodiment similar to the ball and socket attachment means, a hinge attachment means is shown in FIG. 22. In this attachment means a cylinder 38a is snapped into a cylindrical socket 40a forming a hinge joint. This hinge joint can attach either the nose piece 14 and the head band 22 or both to the shield 10. The hinge joints on the shields 10 for attaching the nose piece 14 must be aligned so that they are mirror images of each other. This hinge joint attachment means allows limited movement of the nose piece 14 and head band 22, while not disturbing the positioning of the shields 10 over the patient's eyes. In an alternative to this attachment means, the socket 40a can be located on the nose piece 14 and head band 22, while the cylinder 38a is located on the shield 10.

Figure 8:
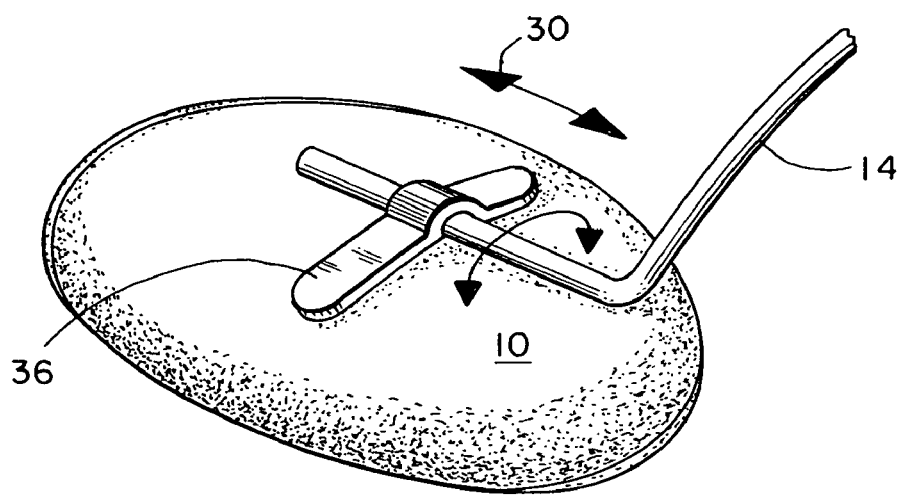
FIG. 8 is a perspective view of a metal strip mounting means.

Another alternative mounting for attaching the nose piece 14 to the shields 10 is shown in FIG. 8. As shown, a strip of material 36, preferably metal, is attached to the surface of the shield 10. The strip 36 is formed so as to provide a space between it and the shield 10 for insertion of the nose piece 14. The strip 36 on the first shield 10 is positioned parallel to the strip 36 on the second shield 10, and the space beneath the first strip 36 is positioned parallel to the space beneath the second strip 36. This alignment allows the nose piece 14 to be moved upwardly or downwardly while the shields 10 remain in a stationary position. The shields 10 can also adjust linearly along the nose piece 14 to adjust the size of the device to fit the patient's anatomy.

Figure 4:
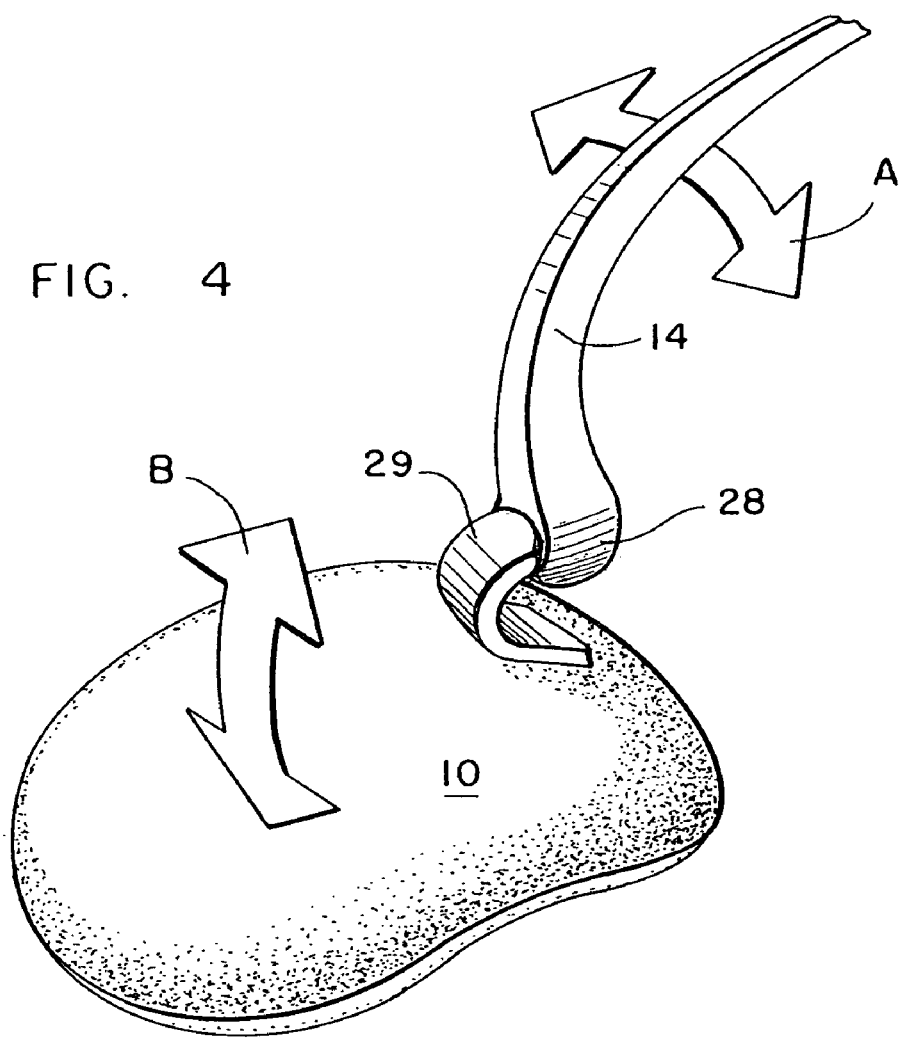
FIG. 4 is a perspective view of a living hinge mounting means.

Yet another mounting means for attaching the nose piece 14 to the shields 10 is shown in FIG. 4. This mounting means provides a living hinge 28 that allows the secure attachment of the nose piece 14 to the shield 10, yet is flexible enough to allow the nose piece 14 to move about the hinge 28. The living hinge 28 on the first shield 10 is aligned parallel to the hinge 28 on the second shield, so that movement of nose piece 14 does not move the shields 10. In this embodiment, the living hinge 28 provides movement of the nose piece 14 as shown by arrow A, and the flexible mounting 29 provides limited movement of the nose piece 14 for minor size adjustments as shown by arrow B. This allows maximum adjustability of the shields 10 so that the device can fit different sized faces.

Figure 17:
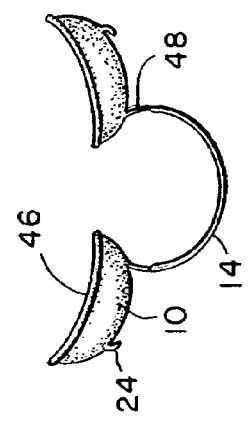
FIG. 17 is a perspective view showing an alternative attachment means wherein the nose piece is flexible and connects directly to the shield using a thin area near the shield.

Yet another means for attaching the nose piece 14 to the shields 10 and allowing adjustability is shown in FIG. 17 wherein the nose piece 14 contains a thin area 48 that allows some flexibility to the nose piece 14. This allows flexibility to the shields 10 while still providing a stable and stationary fit to the patient's face and eyes.

It is important that all embodiments of the present invention be adjustable so that the ocular shield device can fit onto different sized faces. The arrows 30 in FIGS. 2 and 8 show how the shields 10 can move linearly by sliding the nose piece 14 through the hole. This allows the shields 10 to adjust linearly along the nose piece 14 so that they can fit the facial anatomy of patients with different sized faces. In the preferred embodiment, each shield 10 can slide about 5 mm (2.5 mm in each direction). FIG. 2 shows how the small flanges 26 protrude from the nose piece 14 to allow the nose piece 14 to move through the post hole 18 a certain distance, while preventing the nose piece 14 from becoming detached from the post 16. To further aid in adjusting the ocular shield device to different sized faces, the nose piece 14 may be made of a more or less flexible metal or plastic.

Figure 5:
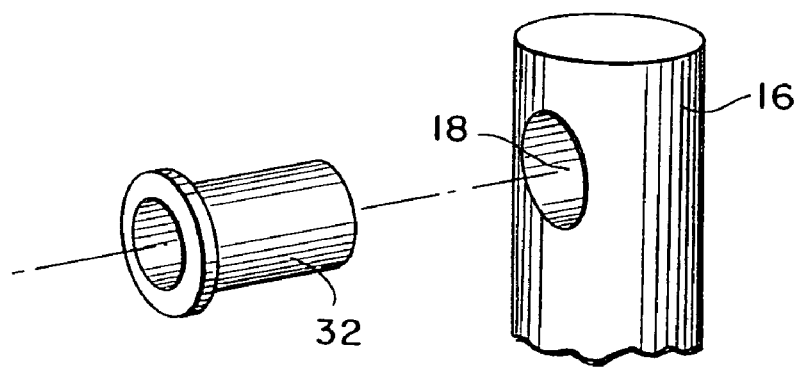
FIG. 5 is a perspective view of a bushing that fits in the post hole.
Figure 6:
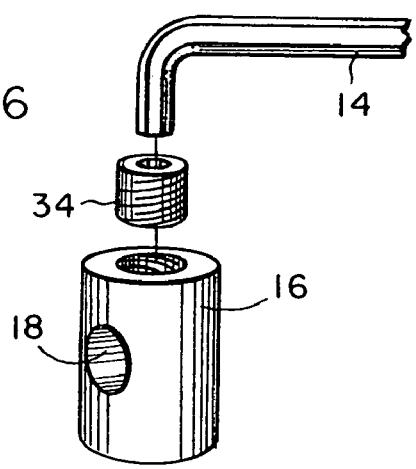
FIG. 6 is a perspective view of a set screw that fits in the post.
Figure 7:
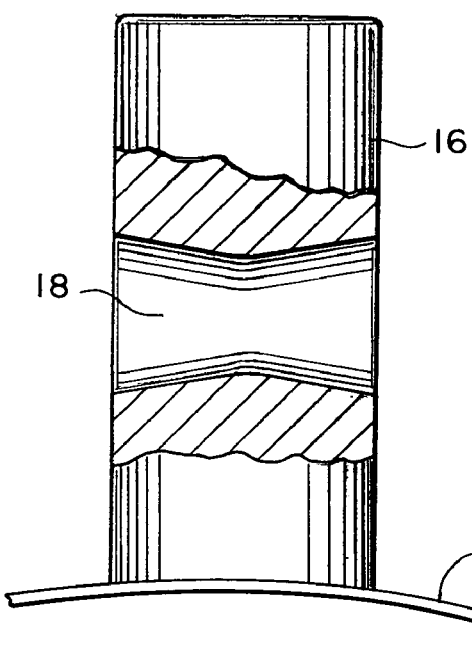
FIG. 7 is a perspective view of a conical post hole.

The nose piece 14 must be capable of being adjusted, yet still retain enough friction with the post 16 so as to only move when desired. FIG. 3 shows the preferred method for achieving this result in which a small elastic band 20 or elastic O-ring is wrapped around the post 16 and the nose piece 14. In this regard, the elastic band 20 is tight enough to keep the shields 10 from moving involuntarily, yet the elastic band 20 is flexible enough to allow voluntary movement of the nose piece 14 upward or downward, and voluntary movement of the shields 10 linearly along the nose piece 14 as shown by the arrows 30 in FIG. 2. Other methods for providing adjustability of the ocular shield by providing the proper amount of friction between the nose piece 14 and the post 16 include: providing a bushing 32 or plastic plug in the post hole 18 as shown in FIG. 5, providing a set screw 34 in the post 16 that contacts the nose piece 14 as shown in FIG. 6, constructing the post hole 18 in a conical shape so as to provide extra adjustability of the shields 10 in relation to the nose piece 14 as shown in FIG. 7.

Figure 10:
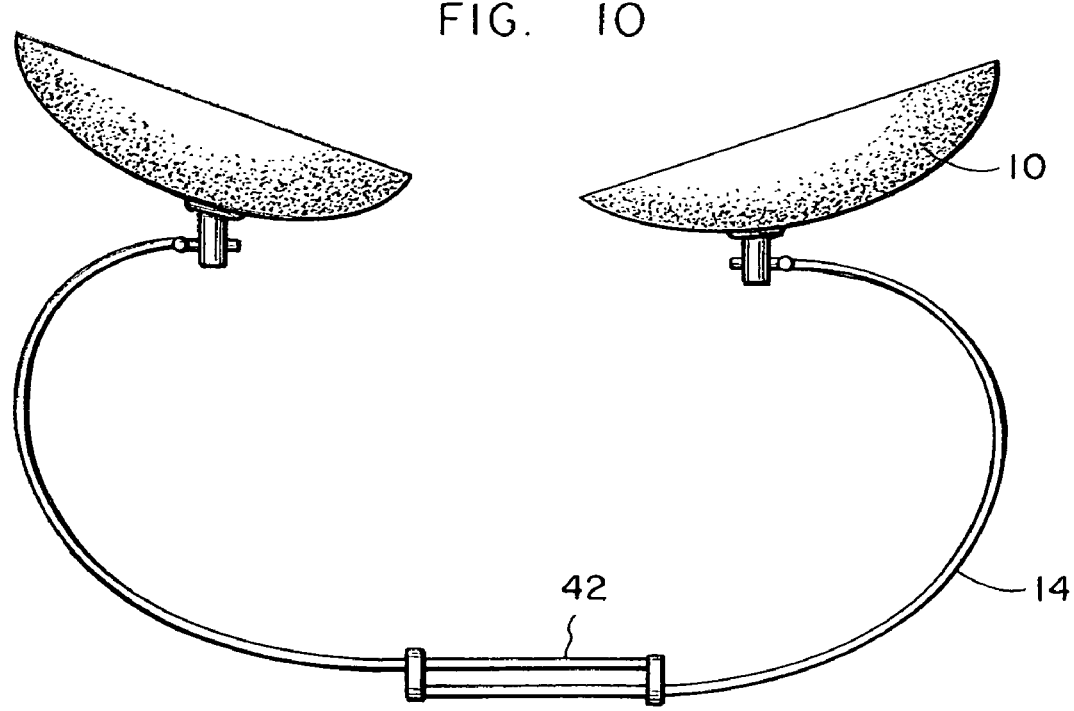
FIG. 10 is a perspective view of a telescoping adjustment mechanism in the nose piece.
Figure 11:
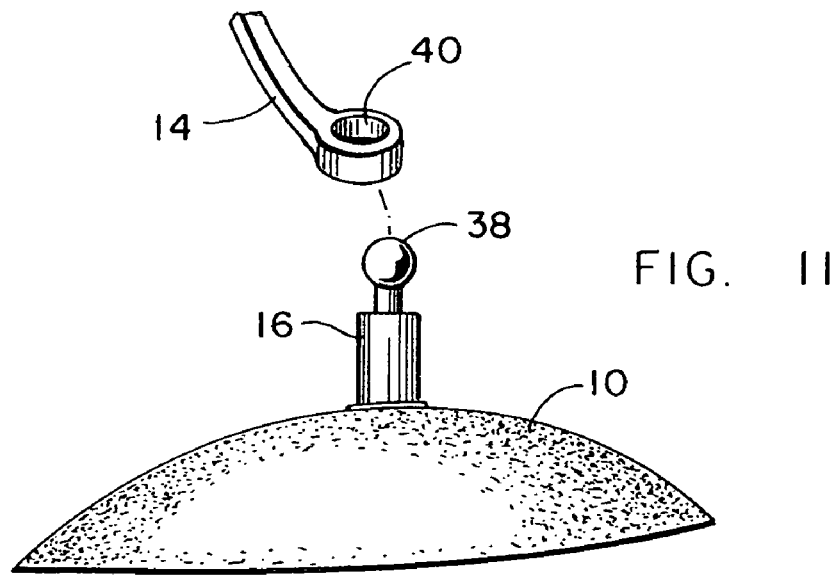
FIG. 11 is a perspective view of a ball and socket mounting means with the ball on the shield and the socket on the nose piece.
Figure 12:
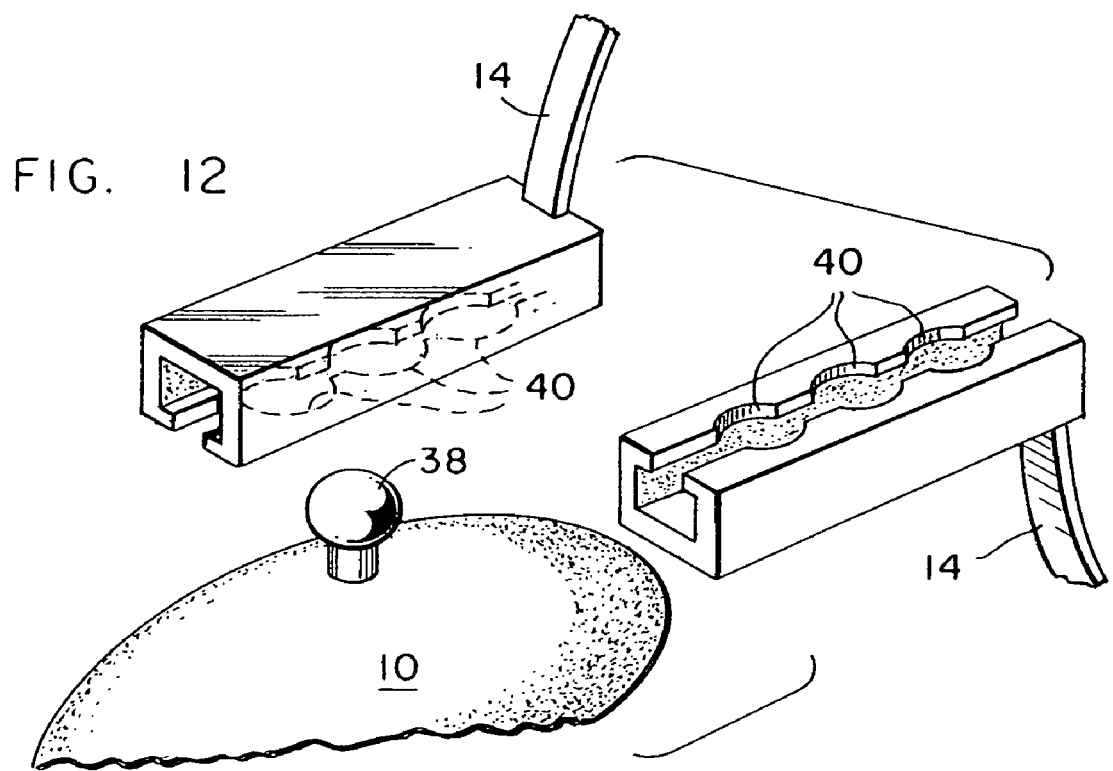
FIG. 12 is a perspective view of a variation of the ball and socket mounting means with multiple sockets on the nose piece for maximum adjustability.

Yet another means for providing adjustability to the ocular shield device is for the nose piece 14 to have a telescoping adjustment 42 as shown in FIG. 10. Using this telescoping adjustment 42, the nose piece 14 no longer slides through the post hole 18 linearly because the size adjustment is provided by the telescoping of the nose piece 14 relative to itself. The telescoping adjustment means is particularly suited for use with a mounting means such as the living hinge, in which adjustment for the distance between the patient's eyes may be more difficult to achieve.

Another embodiment of the invention comprises an ocular shield device in which metal shields 10 have been coated with plastic. The coating insulates the metal from any heat source or radio frequency current that would otherwise heat the metal and burn the tissue touching the shields 10. This embodiment contains many of the concepts previously stated in the above embodiments as to mounting, adjustability, fit, and precise movement of the nose piece 14 without moving the shields 10.

Figure 18:
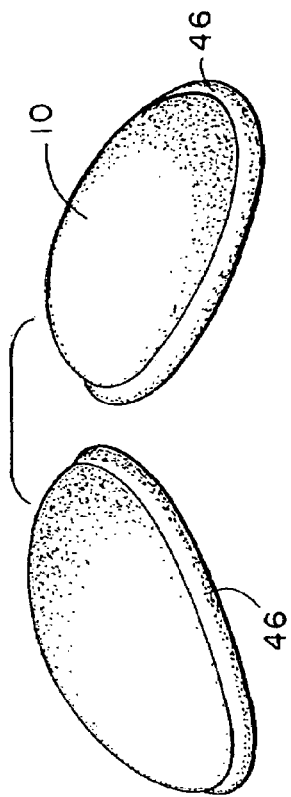
FIG. 18 is a perspective view of shields showing the elastomeric lip.

Another embodiment of the invention comprises an ocular shield device in which the shields 10 are made entirely of plastic. These plastic shields 10 contain many of the concepts previously stated in the above embodiments as to mounting, adjustability, fit, and precise movement of the nose piece 14. This embodiment can comprise any of the attachment means discussed above as well as no attachment means, where the nose piece 14 attaches directly to the shields 10. In this direct attachment, the adjustability of the device is provided only by the flexibility of the plastic nose piece 14, as shown in FIG. 17 and described above. The shields 10 in this embodiment are plastic so that they do not feel as hot to the touch if they are exposed to long periods of radiation, such as in a tanning bed or radio frequency energy or dermabrasion systems. In this embodiment the plastic nose piece 14 extends generally outwardly from the shields 10 so that it will not conceal any area of the face or make a shadow on the face, when such shadow is not desired. A rubber or elastomeric lip 46, as seen in FIG. 18, can be molded onto the plastic shields 10 so as to provide a comfortable and precise fit around the patient's eyes. This elastomeric lip 46 can be permanently molded onto the shield 10, or it can be made to be removable and replaced after each use.

Within the plastic shield embodiment, it is possible for the shields to be either opaque or transparent, as long as the energy is blocked by the correct tint of the shields 10. Transparent shields offer some vision to the patient while the patient is wearing the shields, which is particularly useful if the patient is claustrophobic.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is:

1. An external protective device for protecting the eyes and the eye lids of a patient against radiation energy, said device comprising:
   a first shield and a second shield, each of which has an inner end and an outer end and is of sufficient size to cover an eye of the patient;
   each shield being made of a material that can block radiation energy;
   a nose piece joining the shields together in a spaced apart relationship so as to position the shields over the eyes of the patient, the nose piece being movable from a first position to a second position; and
   a mounting on each shield for attaching the nose piece to the shield wherein the nose piece can move from the first position to the second position while the device is covering the patient's eyes without altering the position of the shields over the patient's eyes.

2. The protective device of claim 1 wherein each mounting has a hole for receiving the nose piece, and the hole in the mounting on the first shield is substantially parallel to the hole in the mounting on the second shield.

3. The protective device of claim 2 wherein the mounting is a strip of material with both ends connected to the shield.

4. The protective device of claim 2 wherein the mounting is a post.

5. The protective device of claim 4 wherein an elastic band is combined with the post to retard involuntary movement of the nose piece relative to the post, while still allowing voluntary movement.

6. The protective device of claim 4 wherein a bushing is combined with the hole in the mounting to retard involuntary movement of the nose piece relative to the post, while still allowing voluntary movement.

7. The protective device of claim 4 wherein a set screw is combined with the mounting to retard involuntary movement of the nose piece relative to the post, while still allowing voluntary movement.

8. The protective device of claim 4 wherein the hole is a conical shaped hole to allow the nose piece to move slightly within the mounting.

9. The protective device of claim 4 wherein a plastic plug is combined with the hole in the mounting to retard involuntary movement of the of the nose piece relative to the post, while still allowing voluntary movement.

10. The protective device of claim 1 wherein the mounting comprises a living hinge.

11. An external protective device for protecting the eyes and the eye lids of a patient against radiation energy, said device comprising:

a first shield and a second shield, each of which has an inner end and an outer end and is of sufficient size to cover an eye of the patient;

each shield being made of a material that can block radiation energy;

a nose piece joining the shields together in a spaced apart relationship so as to position the shields over the eyes of the patient, the nose piece being movable from a first position to a second position; and a mounting on each shield for attaching the nose piece to the shield wherein the nose piece can move from the first position to the second position without altering the position of the shields;

wherein the mounting comprises a ball and a socket that together form a ball and socket joint for connecting the nose piece to the shield.

12. The protective device of claim 11 wherein the socket is on the shield and the ball is on the nose piece.

13. The protective device of claim 11 wherein the ball is on the shield and the socket is on the nose piece.

14. The protective device of claim 11 wherein a plastic member is positioned in the socket and engages the ball to provide a better fit of the ball into the socket.

15. The protective device of claim 11 wherein the socket is comprised of two pieces that attach around the ball of the ball and socket joint by fastening together.

16. The protective device of claim 11 wherein the socket is comprised of two pieces that attach around the ball of the ball and socket joint by screwing together.

17. The protective device of claim 11 wherein multiple balls are provided to allow for adjustability.

18. The protective device of claim 11 wherein multiple sockets are provided to allow for adjustability.

19. The protective device of claim 1 further comprising a headband member that is connected to each shield and adapted to be placed around and behind the patient's head to hold the shields over the patient's eyes.

20. The protective device of claim 19 wherein the headband member is adjustable and removable from the device for separate sterilization.

21. The protective device of claim 19 wherein a ball and a socket joint combines the headband member with each shield.

22. The protective device of claim 21 wherein the ball is on the shield and has a notch adapted for the insertion of an elastic headband member.

23. The protective device of claim 19 wherein the headband member is made of elastic.

24. The protective device of claim 1 wherein the shields are made of stainless steel.

25. The protective device of claim 1 wherein the shields are made of plastic.

26. The protective device of claim 25 wherein the shields are at least partially transparent.

27. The protective device of claim 1 wherein the shields are coated with plastic.

28. The protective device of claim 1 wherein the nose piece is combined directly with the shield.

29. The protective device of claim 1 wherein the nose piece further comprises a telescoping adjustment mechanism.

30. The protective device of claim 4 wherein the nose piece further comprises flanges that limit the travel of the nose piece relative to the mounting.

31. The protective device of claim 1 wherein an elastomeric lip is molded onto the shields so as to provide a precise fit around the patient's eyes.

32. The protective device of claim 1 in which the shields have an outer surface that is non-reflective.

33. The protective device of claim 1 wherein the mounting comprises a hinge joint.

* * * * *